United States Patent
Shuber et al.

(10) Patent No.: US 6,214,558 B1
(45) Date of Patent: Apr. 10, 2001

(54) METHODS FOR THE DETECTION OF CHROMOSOMAL ABERRATIONS

(75) Inventors: Anthony P. Shuber, Milford, MA (US); Stanley N. Lapidus, Bedford, NH (US)

(73) Assignee: Exact Laboratories, Inc., Maynard, MA (US)

(*) Notice: Subject to any disclaimer, the term of this patent is extended or adjusted under 35 U.S.C. 154(b) by 0 days.

(21) Appl. No.: 09/626,809

(22) Filed: Jul. 27, 2000

Related U.S. Application Data

(63) Continuation of application No. 08/984,856, filed on Dec. 4, 1997, now Pat. No. 6,100,029, which is a continuation-in-part of application No. 08/876,857, filed on Jun. 16, 1997, now Pat. No. 5,928,870, which is a continuation-in-part of application No. 08/700,583, filed on Aug. 14, 1996, now Pat. No. 5,670,325.

(51) Int. Cl.$^7$ ................................................ C12Q 1/68
(52) U.S. Cl. ................................. 435/6; 536/23.3
(58) Field of Search ................................ 435/6; 536/23.3

(56) References Cited

PUBLICATIONS

Bos et al., Nature 327:293–97, May 1978.*

* cited by examiner

*Primary Examiner*—Scott W. Houtteman
(74) *Attorney, Agent, or Firm*—Testa, Hurwitz & Thibeault, LLP

(57) ABSTRACT

Methods are provided for detecting fetal chromosomal aberrations by detecting statistically-significant differences between normal and aberrant chromosomes.

1 Claim, 3 Drawing Sheets

METHODS FOR THE DETECTION OF CHROMOSOMAL ABERRATIONS

This application is a Continuation of Ser. No. 08/984,856 filed Dec. 4, 1997, now U.S. Pat. No. 6,100,029 which is Continuation-In-Part of U.S. Ser. No. 08/876,857, filed Jun. 16, 1997, now U.S. Pat. No. 5,928,870 which is a Continuation-In-Part of U.S. Ser. No. 08/700,583 filed Aug. 14, 1996, now U.S. Pat. No. 5,670,325.

FIELD OF THE INVENTION

This invention provides methods useful for disease diagnosis by detecting chromosomal aberrations in tissue or body fluid samples. Methods of the invention are especially useful in detecting fetal chromosomal aberrations in blood or in amniotic fluid.

BACKGROUND OF THE INVENTION

Typically, prenatal diagnostic tests include fetal karyotype analysis. Traditional methods rely on invasive techniques, such as amniocentesis and chorionic villus sampling, both of which incur some risk of fetal injury or loss. See, e.g., Sundberg, et. al., Lancet, 350: 697–703 (1997). As an alternative to sampling the fetal environment, current techniques often involve isolating fetal cells from maternal blood. See, e.g., Liou, et al., *Ann. N. Y. Acad. Sci.*, 7: 237–241 (1994). Nucleated red blood cells are reported to be a good cell type for analysis because those cells have sufficient DNA for analysis, they are present in maternal blood, they are easily identified based on their morphology, and they have a known gestational life span. Lamvu, et al., *Obstet. Gynecol. Surv.*, 52: 433–437 (1997).

Whether taken from chorionic villi, amniotic fluid, or maternal blood, samples commonly are karyotyped to determine chromosomal abnormalities, such as aneuploidies. Cytogenic techniques with high-resolution banding frequently have been used for diagnosis of gross fetal chromosomal abnormalities. However, small chromosomal abnormalities (i.e., those involving changes of less than about 5 million base pairs) are difficult, if not impossible, to detect using gross cytogenetic tests. Accordingly, preferred techniques for diagnosis of both gross abnormalities and smaller nucleic acid mutations include molecular cytogenetic techniques, such as fluorescence in situ hybridization (FISH). For example, fetal cells from maternal blood have been isolated using density gradient centrifugation, and magnetic cell sorting, and counted using FISH. Jansen, et al., *Prenat. Diagn.*, 17(10): 953–959 (1997). The FISH technique, either alone, or in conjunction with fluorescent polymerase chain reaction, has become a primary technique for diagnosis of prenatal genetic abnormalities in samples from chorionic villi, amniotic fluid, blood, and whole cells, obtained, for example, from transcervical sampling. While FISH is adequate for screening for common chromosomal aneuploidies, such as trisomy 21, trisomy 13, XXY, and monosomy X, it is not useful for detecting chromosome deletions or rearrangements, which are common in, for example, chromosomes 12, 14, and 17. Lamvu, supra.

Accordingly, further techniques are necessary and desirable for detecting fetal chromosomal abnormalities. Such techniques are presented herein.

SUMMARY OF THE INVENTION

The present invention provides methods for detecting and diagnosing fetal chromosomal aberrations. Methods of the invention comprise detecting in a tissue or body fluid sample, a statistically-significant variation in fetal chromosome number or composition. Practice of the invention permits, for example, detection of aneuploidies, as well as partial chromosomal deletions, nucleic acid substitutions, rearrangements, additions, and the like. A preferred use of the methods is to reliably detect a fetal chromosomal aberration in a chorionic villus sample, amniotic fluid sample, maternal blood sample, or other tissue or body fluid. A fetal chromosomal aberration may be a reduction in chromosome number (e.g., XO), an increase in chromosome number (e.g., XXY, trisomy 21), a chromosomal translocation, a chromosomal deletion (e.g., loss of heterozygosity), or a chromosomal rearrangement. The invention takes advantage of several important insights which permit, for example, reliable detection of a chromosomal deletion or addition. Methods of the invention are useful for the detection and diagnosis of a nucleic acid abnormality, such as a loss of heterozygosity or, more generally, a gross chromosomal abnormality. Detection of such abnormalities may be indicative of a fetal disease or a developmental abnormality (e.g., proper morphological development, proper metabolic development, etc.).

For purposes of the present invention, unless the context requires otherwise, a "mutation" includes modifications, rearrangements, deletions, substitutions, and additions in a portion of genomic DNA or its corresponding mRNA.

In general, the invention comprises methods for counting (i.e. enumerating) the number of a target fetal chromosomal nucleic acid present in a sample. That number is compared with the number of a reference fetal chromosomal nucleic acid. The reference nucleic acid number may be determined from within the sample, or may be an external standard representing the numerical range considered to be indicative of a normal, intact karyotype (i.e., a diploid number of chromosomes). Methods of the invention determine whether any difference between the number of target and reference nucleic acids is statistically significant, a statistically significant difference being indicative of a fetal chromosomal abnormality.

A useful reference number of a nucleic acid is the number of molecules of a reference nucleic acid chosen such that the numbers of molecules of the target and reference nucleic acids are identical in normal fetal cells (i.e., cells not having an aneuploidy or mutation). The enumerative methods of the invention are useful to identify a statistically-significant difference between quantities of target and reference nucleic acids, and to correlate any difference, to a degree of defined statistical confidence, with the presence in the sample of an aneuploidy or mutation.

In a preferred embodiment, an enumerative amount (number of copies) of a target nucleic acid (i.e., chromosomal DNA or portion thereof) in a sample is compared to an enumerative amount of a reference nucleic acid. The reference number is determined by a standard (i.e., expected) amount of the nucleic acid in a normal karyotype or by comparison to a number of a nucleic acid from a non-target chromosome in the same sample, the non-target chromosome being known or suspected to be present in an appropriate number (i.e., diploid for the autosomes) in the sample. A statistically-significant difference between the two enumerative amounts is indicative of an aneuploidy or mutation in the target chromosome.

Also in a preferred general embodiment of the invention, an enumerative amount of a maternal allele on a chromosome is compared to an enumerative amount of the corresponding region of a paternal allele on the same chromosome. A statistically-significant difference between the two amounts is indicative of an aneuploidy or mutation in the chromosome.

In a preferred embodiment, enumerative detection of a chromosomal aberration is accomplished by exposing a nucleic acid sample to first and second radionucleotides. The radionucleotides may be single nucleotides or oligonucleotide probes. The first radionucleotide is capable of hybridizing to a target fetal chromosomal region (i.e., on a chromosome suspected to contain an aberration). The second radionucleotide is capable of hybridizing to a region of a reference fetal chromosome known not to contain an aberration. After washing to remove unhybridized radionucleotides, the number of each of first and second radionucleotides is counted. A statistically-significant difference between the number of first and second radionucleotides is indicative of a the fetal chromosomal abnormality. In a highly-preferred embodiment, fetal chromosomal material is isolated from maternal and other material prior to the exposing steps. Also in a highly-preferred embodiment, the number of the fetal chromosomal region is compared to a predetermined reference standard that provides a range of normal values. A target number within the range is indicative of a "normal" chromosome number for the target (i.e., the chromosome contains aneuploidies).

In preferred methods of the invention, first and second radionucleotides are isolated from other sample components by, for example, gel electrophoresis, chromatography, and mass spectrometry. Also in a preferred embodiment, either or both of the first and second radionucleotides is a chain terminator nucleotide, such as a dideoxy nucleotide. A preferred radionucleotide for use in methods of the invention is selected from the group consisting of $^{32}P$, $^{33}P$, $^{35}S$, $^{3}H$, $^{125}I$, and $^{14}C$. The number of first and second radionucleotides may be determined by counting.

Also in a preferred embodiment, chromosomes or chromosomal material may be counted by using nucleic acid probes attached to high molecular weight particles or beads. Upon hybridization and washing, the particles attached to hybridized probes are counted in a Coulter counter or other similar device, as, for example, taught in U.S. Pat. No. 5,670,325, incorporated by reference herein.

The present invention provides methods for detecting genomic changes in fetal chromosomes, wherein the chromosomal aberration represents a small subpopulation in a heterogeneous biological sample. Methods of the invention may be performed on any biological sample, including tissue and body fluid samples. Particularly preferred biological samples include amniotic fluid, chorionic villi, and blood. Methods of the invention may be practiced by exposing a sample to one or more radionucleotides in order to separately detect the number X of a first polynucleotide representing a first fetal chromosome and the number Y of a second polynucleotide representing a second fetal chromosome. In a preferred embodiment the radionucleotides are incorporated into oligonucleotide probes which are exposed to the sample under conditions that promote specific hybridization of the radiolabeled oligonucleotide probes with the first or second polynucleotides. In a highly preferred embodiment, first and second unlabeled oligonucleotide primers are exposed to the sample. A first primer hybridizes to at least a portion of a first chromosome (i.e., chromosomal DNA), and a second primer hybridizes to at least a portion of a second chromosome. The probes are subsequently radiolabeled using a primer extension reaction in the presence of added radiolabeled nucleotides. Preferably, the primer extension reaction is a single base extension reaction using chain terminating nucleotides, (e.g. dideoxynucleotides). If the sequence of the portion of each chromosome to which the primers hybridize is known, different chain-termination nucleotides are used and counted separately. The different chain-termination nucleotides are differentially labeled (i.e., with different isotopes, with molecular weight markers, color markers, or any combination thereof). A statistically-significant difference in the number of the different (in this case two) chain-terminating nucleotides is indicative of a chromosomal aberration in one of the chromosomes, typically the one suspected to have an aberration. Further cytologic testing is done to confirm the aberration (e.g., FISH). The number of molecules of a polynucleotide in a sample is calculated from the measurement of the number of radioactive decay events that is specifically associated with the polynucleotide. The number of radioactive decay events is directly proportional to the number of molecules.

In a preferred embodiment the first and second radiolabeled oligonucleotides are separable from each other. For example, the first and second oligonucleotides are of different sizes and can be separated by gel electrophoresis, chromatography or mass spectrometry. In one embodiment the first and second oligonucleotides are of different lengths. In a preferred embodiment the size difference is imparted by a size marker which is specifically attached to one of the two oligonucleotides. Alternatively a different size marker is attached to each oligonucleotide. After separation, the number of radioactive decay events is measured for each oligonucleotide, and the number of molecules is calculated as described herein.

In a highly preferred embodiment, the first and second oligonucleotides are of the same size but are labeled with different radioisotopes selected from, for example, $^{35}S$, $^{32}P$, $^{33}P$, $^{3}H$, $^{125}I$ and $^{14}C$. The first and second oligonucleotides are then distinguished by different characteristic emission spectra. The number of radioactive decay events is measured for each oligonucleotide without separating the two oligonucleotides from each other.

Methods of the invention also may be used to detect a mutation at a fetal allele by determination of the amounts of maternal and paternal alleles comprising a genetic locus that includes at least one single-base polymorphism. A statistically-significant difference in the numbers of each allele is indicative of a mutation in an allelic region encompassing the single-base polymorphism. In this method, a region of an allele comprising a single-base polymorphism is identified, using, for example, a database, such as GenBank, or by other means known in the art. Probes are designed to hybridize to corresponding regions on both paternal and maternal alleles immediately 3' to the single base polymorphism. After hybridization, a mixture of at least two of the four common dideoxy nucleotides are added to the sample, each labeled with a different detectable label. A DNA polymerase is also added. Using allelic DNA adjacent the polymorphic nucleotide as a template, hybridized probe is extended by the addition of a single dideoxynucleotide that is the binding partner for the polymorphic nucleotide. After washing to remove unincorporated dideoxynucleotides, the dideoxynucleotides which have been incorporated into the probe extension are detected by determining the number of bound extended probes bearing each of the two dideoxy nucleotides in, for example, a scintillation counter. The presence of an almost equal number of two different labels mean that there is normal heterozygosity at the polymorphic nucleotide. The presence of a statistically-significant difference between the detected numbers of the two labels means that a deletion of the region encompassing the polymorphic nucleotide has occurred in one of the alleles.

Methods of the invention are useful to detect and diagnose an unlimited array of prenatal genetic abnormalities that affect the number of intact fetal chromosomes. Accordingly, in one aspect the invention provides methods for diagnosis of prenatal genetic abnormalities comprising comparing the number of a chromosome, or a chromosomal region, suspected to contain an aberration with the number of a reference chromosome in the same sample or a standard chromosome number (preferably adjusted by sample volume, weight, or other appropriate means). A statistically-significant difference in the numbers is indicative of a chromosomal aberration (e.g., an aneuploidy) or a mutation Further aspects of the invention will become apparent upon consideration of the following detailed description and of the drawings.

DETAILED DESCRIPTION OF THE INVENTION

Figure 1:
FIG. 1 depicts differential primer extension as exemplified below.
Figure 1:

Methods of the present invention are useful for prenatal diagnosis of fetal genetic abnormalities. These include, inter alia, both aneuploides and chromosomal mutations, such as deletions, additions, rearrangements, translocations, and substitutions in chromosomal DNA.

Methods of the invention comprise comparing the number of a target chromosome, or portion thereof, with a reference number. The reference number is a number of the chromosome expected to be in the sample. The reference number may be derived based upon pre-calculated standards (i.e., by averaging over a large number of normal samples), or may be determined in the sample by comparison with a second, reference number of a second chromosome. In an alternative embodiment, the reference number may be a number of a non-target chromosome in the maternal genome.

In another embodiment, the number of a target chromosome, or portion thereof, may be determined by using a paternally-derived nucleic acid probe. This works if the mother and the father both are homozygous for a different allele (rendering the fetus heterozygous). A probe based upon the paternal allele allows detection of numbers of target and reference chromosomes without separation of fetal and maternal cells.

Enumerative sampling of a nucleotide sequence that is uniformly distributed in a biological sample typically follows a Poisson distribution. For large populations, such as the typical number of genomic polynucleotide segments in a biological sample, the Poisson distribution is similar to a normal (Gaussian) curve with a mean, N, and a standard deviation that may be approximated as the square root of N.

Statistically-significance between numbers of target and reference genes obtained from a biological sample may be determined by any appropriate method. See, e.g., Steel, et al., Principles and Procedures of Statistics, A Biometrical Approach (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between numbers of target and reference genes that must be obtained in order to reach a chosen level of statistical significance. A threshold issue in such a determination is the minimum number, N, of genes (for each of target and reference) that must be available in a population in order to allow a determination of statistical significance. The number N will depend upon the assumption of a minimum number of aberrant chromosomes in a sample (assumed for exemplification to be at least 1%) and the further assumption that normal samples contain no aberrant alleles. It is also assumed that a threshold differences between the numbers of reference and target chromosomes must be at least 0.5% for a diagnosis that there is a chromosomal aberration present in the sample. Based upon the foregoing assumptions, it is possible to determine how large N must be so that a detected difference between numbers of aberrant and normal chromosomes of less than 0.5% is truly a negative (i.e. no mutant subpopulation in the sample) result 99.9% of the time.

Figure 2A:
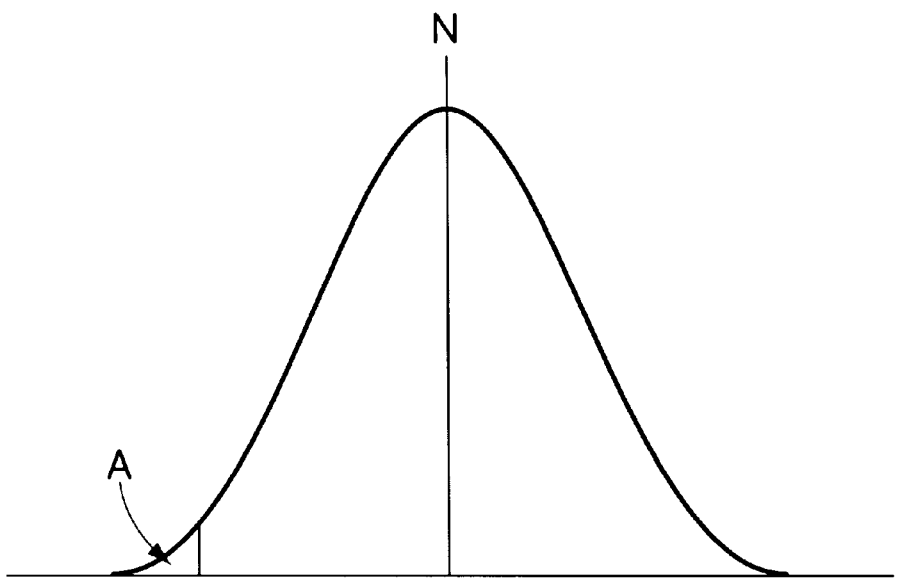
FIGS. 2A and 2B are model Gaussian distributions showing regions of low statistical probability.
Figure 2B:
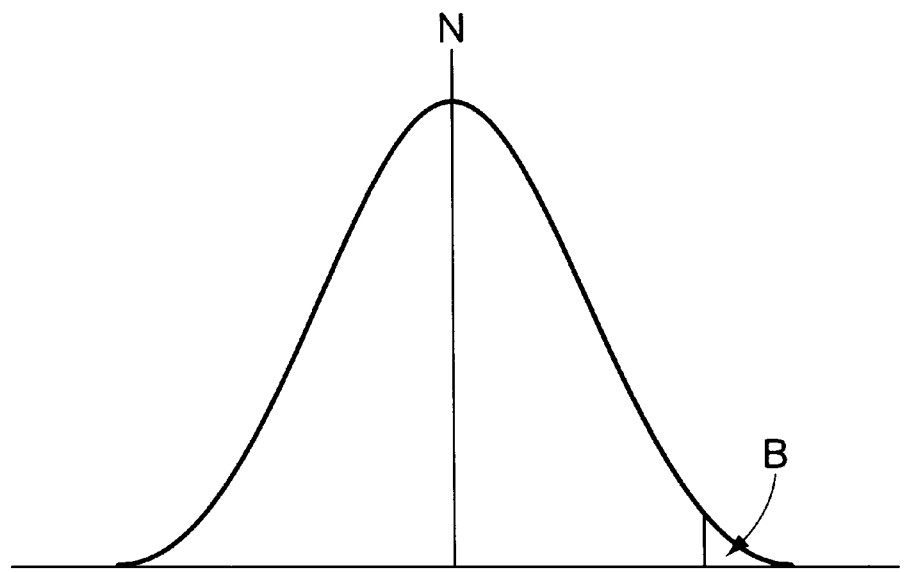

The calculation of N for specificity, then, is based upon the probability of one sample measurement being in the portion of the Gaussian distribution covering the lowest 3.16% of the population (the area marked "A" in FIG. 2A) and the probability that the other sample measurement is in the portion of the Gaussian distribution covering the highest 3.16% of the population (the area marked "B" in FIG. 2B). Since the two sample measurements are independent events, the probability of both events occurring simultaneously in a single sample is approximately 0.001 or 0.1%. Thus, 93.68% of the Gaussian distribution (100%−2×3.16%) lies between the areas marked A and B in FIG. 3. Statistical tables indicate that such area is equivalent to 3.72 standard deviations. Accordingly, 0.5% N is set equal to 3.72 sigma. Since sigma (the standard deviation) is equal to $\sqrt{N}$, the equation may be solved for N as 553,536. This means that if the lower of the two numbers representing reference and target is at least 553,536 and if the patient is truly normal, the difference between the numbers will be less than 0.5% about 99.9% of the time.

Figure 3:
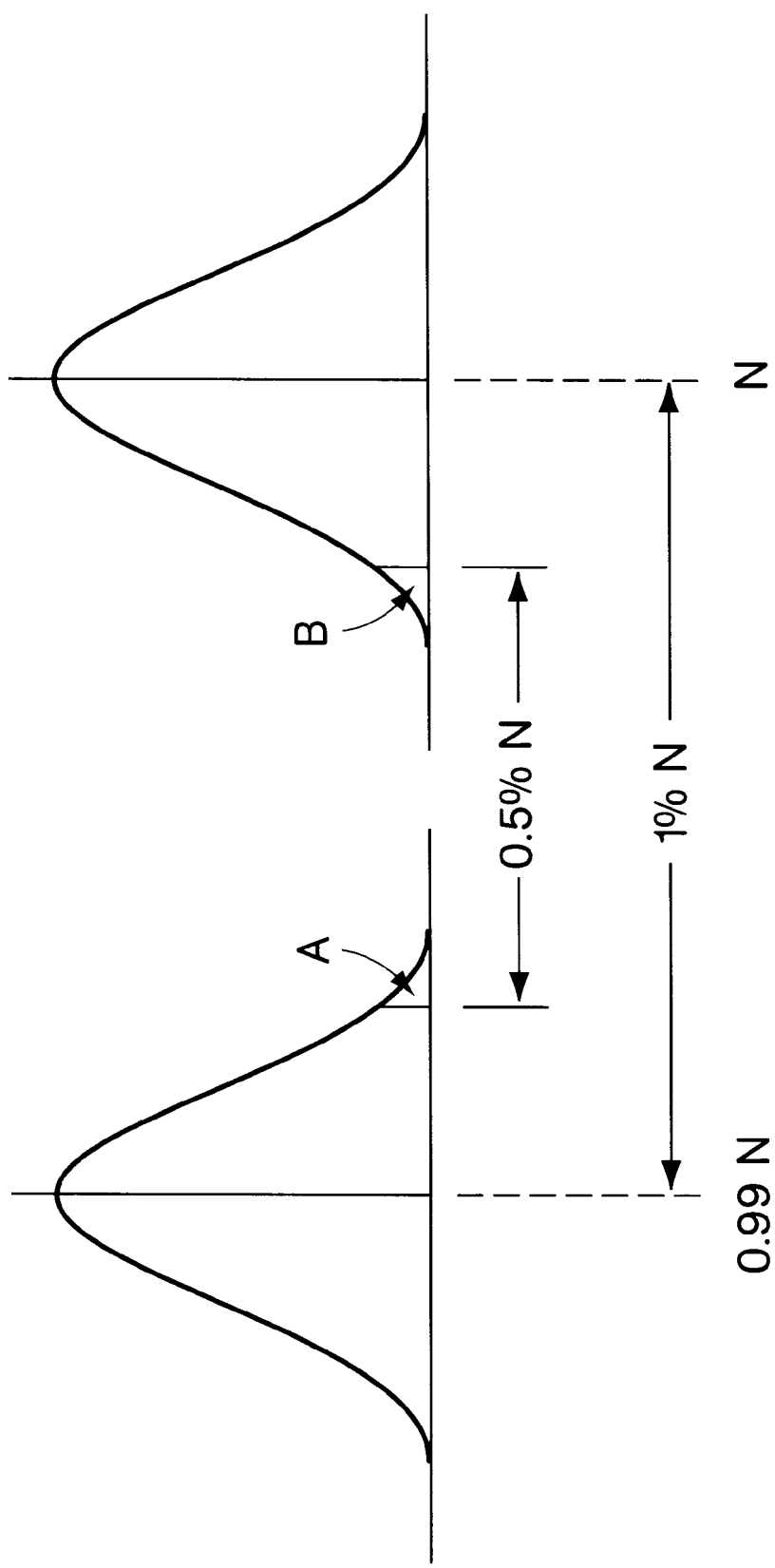
FIG. 3. is a graph showing the probable values of N for a heterogeneous population of cells in which 1% of the cells are mutated.

To determine the minimum N required for 99% sensitivity a similar analysis is performed. This time, one-tailed Gaussian distribution tables show that 1.28 standard deviations (sigma) from the mean cover 90% of the Gaussian distribution. Moreover, there is a 10% (the square root of 1%) probability of one of the numbers (reference or target) being in either the area marked "A" in FIG. 3 or in the area marked "B" in FIG. 3. If the two population means are a total of 1% different and if there must be a 0.5% difference between the number of target and reference genes, then the distance from either mean to the threshold for statistical significance is equivalent to 0.25% N (See FIG. 3) for 99% sensitivity. As shown in FIG. 3, 0.25% N corresponds to about 40% of one side of the Gaussian distribution. Statistical tables reveal that 40% of the Gaussian distribution corresponds to 1.28 standard deviations from the mean. Therefore, 1.28 sigma is equal to 0.0025N, and N equals 262,144. Thus, for abnormal samples, the difference will exceed 0.5% at least 99% of the time if the lower of the two numbers is at least 262,144. Conversely, an erroneous negative diagnosis will be made only 1% of the time under these conditions.

In order to have both 99.9% specificity (avoidance of false positives) and 99% sensitivity (avoidance of false negatives), a sample with DNA derived from at least 553,536 (or roughly greater than 550,000) cells should be counted. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

The foregoing analysis assumes that an aberrant chromosome represents about 1% of that chromosome present in the sample. Typically, however, fetal samples containing an aneuploidy enriched for the aneuploidy (i.e., nearly all of a given chromosome in the sample are affected). In such cases, DNA from fewer than the approximately 500,000 cells indicated above would have to be counted. The precise number of cells is determined based upon the foregoing statistical principles.

Based upon the foregoing explanation, the skilled artisan appreciates that methods of the invention are useful to detect aberrations in fetal chromosome number or fetal chromosomal mutations affecting the number of intact chromosomes.

I. Preparation of Sample

Sample may be prepared from any tissue or body fluid that contains fetal genetic material. Preferred sources are chorionic villi, amniotic fluid, and blood. For purposes of exemplification, samples of fetal genetic material are obtained from amniotic fluid. The fluid is centrifuged at 5,000 rpm for 15 minutes at 4° C. The supernatent is removed, and cells are resuspended in lysis buffer comprising final concentrations of 0.1 M Tris (pH 7.5), 0.8 M NaCl, 20 mM EDTA, 0.2% SDS, 1.mg/ml Proteinase K, and incubated overnight at 37° C. A phenol/chloroform extraction is performed. The DNA is precipitated with 0.1 volume of 3 M NaAc, and an equal volume of isopropanol. The DNA is then centrifuged at 10,000 rpm for 10 minutes at 4° C. The isopropanol is removed, the pellet is dried, and the DNA is resuspended in a Tris-EDTA (10 mM Tris, 1 mM EDTA).

II. Methods for Detection of Chromosomal Abnormalities

For exemplification, methods of the invention are used to detect a trisomy in fetal chromosome 21. Trisomy 21, commonly referred to as Down's Syndrome, results in profound mental and physical disabilities. Samples are prepared as described above. Once DNA is purified from amniotic fluid, it is exposed to one or more detectablylabeled nucleic acid probes. A first probe is capable of hybridizing specifically with a portion of the DNA comprising a portion of fetal chromosome 21. The sequence of the portion of chromosome 21 to which the probe hybridizes is known in order to achieve maximum specificity. Either portions of a coding strand or its complement may be detected in methods of the invention. In a preferred embodiment, both first and second strands of an allele are present in a sample during hybridization to an oligonucleotide probe. The sample is exposed to an excess of probe that is complementary to a portion of the first strand, under conditions to promote specific hybridization of the probe to the portion of the first strand. In a most preferred embodiment, the probe is in sufficient excess to bind all the portion of the first strand, and to prevent reannealing of the first strand to the second strand of the allele. Also in a preferred embodiment, the second strand of an allele is removed from a sample prior to hybridization to an oligonucleotide probe that is complementary to a portion of the first strand of the allele. Preferably, the DNA is amplified by, for example, Polymerase chain reaction (PCR), and/or digested using one or more restriction endonucleases.

For exemplification, detection of the number of a coding strand of a portion of fetal chromosome 21 is described. The number of a coding strand of a portion of fetal chromosome 8 is used as a reference number. Complement to both chromosomes 21 and 8 are removed by hybridization to anti-complement oligonucleotide probes (isolation probes) and subsequent removal of duplex formed thereby. Methods for removal of complement strands from a mixture of single-stranded oligonucleotides are known in the art and include techniques such as affinity chromatography. Upon converting double-stranded DNA to single-stranded DNA, sample is passed through an affinity column comprising bound isolation probe that is complementary to the sequence to be isolated away from the sample. Conventional column chromatography is appropriate for isolation of complement. An affinity column packed with sepharose or any other appropriate materials with attached complementary nucleotides may be used to isolate complement DNA in the column, while allowing DNA to be analyzed to pass through the column. See Sambrook, Supra. As an alternative, isolation beads may be used to exclude complement as discussed in detail below.

After removal of complement, the target and reference nucleic acids are exposed to radio-labeled nucleotides under conditions which promote specific association of the radio-labeled nucleotides with the target and reference nucleic acids in a sample. In order to count the number of molecules of the target and reference nucleic acids, the radionucleotides associated with the target nucleic acid must be distinguished from the radionucleotides associated with the reference nucleic acid. In addition, the radionucleotides that are specifically associated with either target or reference nucleic acid must be distinguished from radionucleotides that are not associated with either nucleic acid. The number of molecules of target nucleic acid is counted by measuring a number X of radioactive decay events (e.g. by measuring the total number of counts during a defined interval or by measuring the time it takes to obtain a predetermined number of counts) specifically associated with the target nucleic acid. The number X is used to calculate the number X1 of radionucleotides which are specifically associated with the target nucleic acid. The number X1 is used to calculate the number X2 of target nucleic acid molecules, knowing the ratio of radionucleotide molecules to target nucleic acid molecules in the assay.

In a preferred embodiment, a radionucleotide is incorporated into a specific oligonucleotide prior to exposure to the sample. In a most preferred embodiment, a radiolabeled oligonucleotide is used which comprises a single radionucleotide molecule per oligonucleotide molecule. A radiolabeled oligonucleotide is designed to hybridize specifically to a target nucleic acid. In one embodiment the target nucleic acid is a specific allele of a polymorphic genetic locus, and the oligonucleotide is designed to be complementary to the allele at the site of polymorphism. One skilled in the art can perform hybridizations under conditions which promote specific hybridization of the oligonucleotide to the allele, without cross hybridizing to other alleles. Similarly, radiolabeled oligonucleotides are designed to specifically hybridize with the reference nucleic acid.

Also in a preferred embodiment, a radionucleotide is specifically incorporated into an oligonucleotide by primer extension, after exposing the oligonucleotide to the sample under conditions to promote specific hybridization of the oligonucleotide with the target nucleic acid. In a preferred embodiment the oligonucleotide is unlabeled, and the radionucleotide is a radiolabeled chain terminating nucleotide (e.g. a dideoxynucleotide). In a most preferred embodiment, the radionucleotide is the chain terminating nucleotide complementary to the nucleotide immediately 5' to the nucleotide that base pairs to the 3' nucleotide of the oligonucleotide when it is specifically hybridized to the target nucleic acid. In the embodiment where the target nucleic acid is an allele of a polymorphic genetic locus, the oligonucleotide is preferably designed such that the 3' nucleotide of the oligonucleotide base pairs with the nucleotide immediately 3' to the polymorphic residue. In a preferred embodiment, a radiolabeled terminating nucleotide that is complementary to the residue at the polymorphic site is incorporated on the 3' end of the specifically hybridized oligonucleotide by a primer extension reaction. Similarly, in a preferred embodiment, a radionucleotide is specifically associated with a reference nucleic acid by primer extension. Other methods for specifically associating a radioactive isotope with a target or reference nucleic acid (for example a radiolabeled sequence specific DNA binding protein) are also useful for the methods of the invention.

In a preferred embodiment, prior to counting the radioactive decay events, the radionucleotides specifically associated with target and reference nucleic acids are separated from the radionucleotides that are not specifically associated with either nucleic acid. Separation is performed as described herein, or using techniques known in the art. Other separation techniques are also useful for practice of the invention. Methods of the invention also comprise distinguishing the radio-label specifically associated with a target nucleic acid from the radio-label specifically associated with a reference nucleic acid. In a preferred embodiment the isotope associated with the target is different from the isotope associated with the receptor. Different isotopes useful to radio-label nucleotides include $^{35}S$, $^{32}P$, $^{33}P$, $^{125}I$, $^{3}H$, and $^{14}C$. In one embodiment, an oligonucleotide complementary to a target nucleic acid is labeled with a different isotope from an oligonucleotide complementary to a reference nucleic acid. In another embodiment, the chain terminating nucleotide associated with the target nucleic acid is different from the chain terminating nucleotide associated with the reference nucleic acid, and the two chain terminating nucleotides are labeled with different isotopes.

In a preferred embodiment, radionucleotides labeled with different isotopes are detected without separating the radionucleotide associated with the target nucleic acid from the radionucleotide associated with the reference nucleic acid. The different isotopes useful to the invention have different characteristic emission spectra. The presence of a first isotope does not prevent the measurement of radioactive decay events of a second isotope. In a more preferred embodiment, the labeled oligonucleotide associated with the target nucleic acid is the same size as the labeled oligonucleotide associated with the reference nucleic acid (the labeled oligonucleotides can be labeled prior to hybridization or by primer extension). The two differentially labeled oligonucleotides are electrophoresed on a gel, preferably a denaturing gel, and the gel is exposed to an imager that detects the radioactive decay events of both isotopes. In this embodiment the two isotopes are detected at the same position on the imager, because both oligonucleotides migrate to the same position on the gel. Detection at the same position on the imager reduces variation due to different detection efficiencies at different positions on the imager.

Also in a preferred embodiment, the radionucleotide associated with the target nucleic acid is separated from the radionucleotide associated with the reference nucleic acid prior to measuring radioactive decay events. In a preferred embodiment the separated radionucleotides are labeled with the same isotope.

Preferred separation methods comprise conferring different molecular weights to the radionucleotides specifically associated with the target and reference nucleic acids. In a preferred embodiment, first probes comprise a "separation moiety." Such separation moiety is, for example, hapten, biotin, or digoxigenin. The separation moiety in first probes does not interfere with the first probe's ability to hybridize with template or be extended. In an alternative embodiment, the labeled ddNTPs comprise a separation moiety. In yet another alternative embodiment, both the first probes and the labeled ddNTPs comprise a separation moiety. Following the extension reaction, a high molecular weight molecule having affinity for the separation moiety (e.g., avidin, streptavidin, or anti-digoxigenin) is added to the reaction mixture under conditions which permit the high molecular weight molecule to bind to the separation moiety. The reaction components are then separated on the basis of molecular weight using techniques known in the art such as gel electrophoresis, chromatography, or mass spectroscopy. See, Ausubel et al., *Short Protocols in Molecular Biology*, 3rd ed. (John Wiley & Sons, Inc., 1995); Wu *Recombinant DNA Methodology II*, (Academic Press, 1995).

Also in a preferred embodiment the radionucleotide associated with a first allele of a polymorphic genetic locus is separated from the radionucleotide associated with a second allele of the polymorphic locus by differential primer extension, wherein the extension products of a given oligonucleotide primer are of a different length for each of the two alleles. In differential primer extension (exemplified in FIG. 1) an oligonucleotide is hybridized such that the 3' nucleotide of the oligonucleotide base pairs with the nucleotide that is immediately 5' of the polymorphic site. The extension reaction is performed in the presence of a radiolabeled terminator nucleotide complementary to the nucleotide at the polymorphic site of the first allele. The reaction also comprises non-labeled nucleotides complementary to the other 3 nucleotides. Extension of a primer hybridized to the first allele results in a product having only the terminator nucleotide incorporated (exemplified in FIG. 1A, T* is the labeled terminator nucleotide). Extension of a primer hybridized to the second allele results in a product that incorporates several non-labeled nucleotides immediately 5' to the terminator nucleotide (exemplified in FIG. 1B). The number of non-labeled nucleotides that are incorporated is determined by the position, on the template nucleic acid, of the closest 5' nucleotide complementary to the terminator nucleotide. In an alternative embodiment, differential primer extension comprises a labeled oligonucleotide and a non-labeled terminator nucleotide.

Labeled probes are exposed to sample under hybridization conditions. Such conditions are well-known in the art. See, e.g., Wallace, et al., *Nucleic Acids Res.*, 6:3543–3557 (1979), incorporated by reference herein. First and Second oligonucleotide probes that are distinctly labeled (i.e. with different radioactive isotopes, fluorescent means, or with beads of different size) are applied to a single aliquot of sample. After exposure of the probes to sample under hybridization conditions, sample is washed to remove any unhybridized probe. Thereafter, hybridized probes are detected separately for chromosome 21 hybrids and chromosome 8 hybrids. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is greater than 0.5% difference between the amount of chromosome 21 detected and the amount of chromosome 8 (assuming an appropriate number of chromosomal DNAs are counted), it may be assumed that an alteration in chromosome 21 has occurred. Statistical significance may be determined by any known method. A preferred method is outlined above.

The foregoing is an exemplification of the invention. Practice of the invention embodies equivalents, and the skilled artisan appreciates that variation may be practiced (e.g., chromosomal material from chromosomes other than 21 and 8 may be used.)

What is claimed is:

1. A method for detecting a fetal chromosomal abnormality, comprising the steps of:

a) introducing a first nucleic acid probe to a sample, wherein said first probe is capable of hybridizing to at least a portion of a first fetal chromosome in the sample;

b) introducing a second nucleic acid probe to the sample, wherein said second probe is capable of hybridizing to at least a portion of a second fetal chromosome;

c) washing said sample to remove unhybridized first and second probes;

d) determining a number X of said first probe that is hybridized to said first fetal chromosome or portion thereof;

e) determining a number Y of said second probe that is hybridized to said second fetal chromosome or portion thereof;

f) determining whether a difference exists between number X and number Y, the presence of a statistically-significant difference being indicative of a fetal chromosomal abnormality.

* * * * *